United States Patent [19]
Kominek et al.

[11] Patent Number: 5,225,335
[45] Date of Patent: Jul. 6, 1993

[54] 1,2-DEHYDROGENATION OF STEROIDAL 21-ESTERS WITH *ARTHROBACTER SIMPLEX* OR *BACTERIUM CYCLOOXYDANS*

[75] Inventors: Leo A. Kominek, Portage; Holly J. Wolf, Plainwell; Paula S. Steiert, Lawton, all of Mich.

[73] Assignee: The Upjohn Company, Kalamazoo, Mich.

[21] Appl. No.: 582,954

[22] Filed: Sep. 12, 1989

[51] Int. Cl.$^5$ ............................................. C12P 33/02
[52] U.S. Cl. ..................................... 435/61; 435/830; 435/252.1
[58] Field of Search ........................................ 435/61

[56] References Cited

U.S. PATENT DOCUMENTS

| | | | |
|---|---|---|---|
| 2,822,318 | 2/1958 | Kroll | 195/51 |
| 2,837,464 | 6/1958 | Nobile | 195/51 |
| 2,902,410 | 9/1959 | Weintraub | 195/51 |
| 2,902,411 | 9/1959 | Murray | 195/51 |
| 3,360,439 | 12/1967 | Erickson | 195/51 |
| 3,770,586 | 11/1973 | Kominek | 195/51 |
| 4,524,134 | 6/1985 | Kominek | 435/61 |
| 4,704,358 | 11/1987 | Kominek | 435/61 |

FOREIGN PATENT DOCUMENTS

| | | |
|---|---|---|
| 0127294 | 12/1984 | European Pat. Off. |
| 2123833 | 2/1984 | United Kingdom |
| 2131811 | 6/1984 | United Kingdom |

Primary Examiner—Douglas W. Robinson
Assistant Examiner—Marian Knode
Attorney, Agent, or Firm—Bruce Stein

[57] ABSTRACT

The present invention involves processes for 1,2-dehydrogenation of $\Delta^4$-3-keto $C_{21}$-hemiester steroids of formula (I)

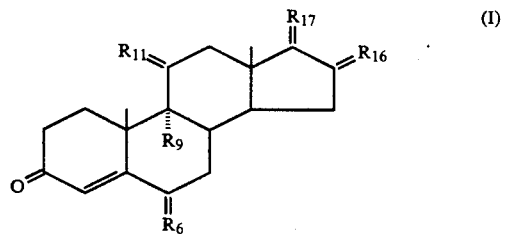

with *Arthrobacter simplex* or *Bacterium cyclooxydans* to produce the corresponding $\Delta^{1,4}$-3-keto $C_{21}$ hemiester of formula (II)

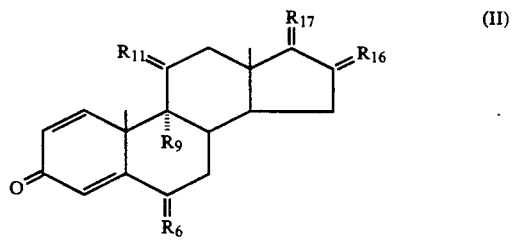

or free alcohol thereof with improved yields. The advantage is that the processes utilize higher substrate concentrations and give shorter reaction times than previously were known.

21 Claims, No Drawings

1,2-DEHYDROGENATION OF STEROIDAL 21-ESTERS WITH *ARTHROBACTER SIMPLEX* OR *BACTERIUM CYCLOOXYDANS*

BACKGROUND OF THE INVENTION

1. Field of the Invention

The present invention involves processes for 1,2-dehydrogenation of certain $\Delta^4$-3-keto $C_{21}$-hemiester steroids with *Arthrobacter simplex* or *Bacterium cyclooxydans* to produce the corresponding $\Delta^{1,4}$-3-keto $C_{21}$ hemiester or free alcohol with improved yields, and shorter bioconversion time.

2. Description of the Related Art

The 1,2-dehydrogenation of $\Delta^4$-3-keto steroids to the corresponding $\Delta^{1,4}$-3-keto steroids with *Septomyxa affinis*, *A. simplex* and other microorganisms is well known in the art and has valuable commercial significance.

U.S. Pat. No. 2,837,464 claims a process for 1,2-dehydrogenation of $\Delta^4$-3-ketopregnenes to $\Delta^{1,4}$-pregnadienes where the $C_{21}$ hydroxyl group is either free or esterified with a monocarboxylic acid by the use of *Corynebacterium (Arthrobacter) simplex* or *Corynebacterium hoagii*.

U.S. Pat. Nos. 2,902,410 and 2,902,411 claim processes for the 1,2-dehydrogenation of 1,2-saturated steroids to 1,2-dehydro steroids with *Septomyxa affinis*.

U.S. Pat. No. 3,360,439 discloses a process for the 1,2-dehydrogenation of $\Delta^4$-3-keto steroids to the corresponding $\Delta^{1,4}$-3-keto steroids using *A. simplex* cells which had been previously treated with a lower alkanol or alkanone. The process of the present invention does not require pretreatment of the cells and may be performed using viable cells in a fermentation broth. Alternatively cells pretreated by air or heat drying or by exposure to a lower alkanone such as acetone may be used. The steroid-1-dehydrogenase of these organisms can also be used in a cell-free form.

U.S. Pat. No. 3,770,586 claims an improved process for the production of 11$\beta$,21-dihydroxypregna-1,4,17(20)-trien-3-one (Example 1) and 11$\beta$,21-dihydroxy-6$\alpha$-methylpregna-1,4,17(20)-trien-3-one (Example 5) whereby the alkali metal salts of the $\Delta^4$-3-keto 21-hemiester substrates thereof where the acyl radical is that of a dicarboxylic acid of 3 to 12 carbon atoms are 1,2-dehydrogenated by use of *S. affinis*. Using shake flasks, 11$\beta$,21-dihydroxypregna-4,17(20)-dien-3-one 21-hemisuccinate potassium salt at a concentration of 5.0 g/l and medium 1, the desired $\Delta^{1,4}$-product was produced in 100% yield after 5 days (Example 8). Example 1 uses larger stirred tanks and shows a lower yield. With medium 2, and 2.0-7.0 g/l of 11$\beta$,21-dihydroxypregna-4,17(20)-dien-3-one 21-hemisuccinate potassium salt yields of 91.1-96.6% were obtained in 6 days.

U.S. Pat. Nos. 4,524,134 and 4,704,358 disclose improved microbial processes to produce a 1,2-dehydrogenated steroid from the corresponding 1,2-saturated $\Delta^4$-3-keto-steroid using air-dried or heat-dried cells of *Arthrobacter simplex* and *Bacterium cyclooxydans* respectively.

The processes of the present invention provide improved yields and at the same time permit the use of higher substrate concentrations and reduced reaction times.

SUMMARY OF THE INVENTION

Disclosed is a process for the production of a $\Delta^{1,4}$-3-keto 21-hemiester steroid (II) where (B-I) $R_6$ is $=CH_2$ or $\alpha$-$R_{6-1}$:$\beta$-H where $R_{6-1}$ is —H, —F and —CH$_3$, $R_7$ is $\alpha$-H:$\beta$-H;

(B-II) $R_6$ is $R_{6-3}$:$R_{6-4}$ and $R_7$ is $R_{7-3}$:$R_{7-4}$ where one of $R_{6-3}$ and $R_{6-4}$ taken together with one of $R_{7-3}$ and $R_{7-4}$ form a second bond between $C_6$ and $C_7$, the other of $R_{6-3}$ and $R_{6-4}$ is —CH$_3$ and the other of $R_{7-3}$ and $R_{7-4}$ is —H;

(C-I) $R_{11}$ is $\alpha$—$R_{11-1}$:$\beta$-$R_{11-2}$ where one of $R_{11-1}$ and $R_{11-2}$ is taken together with $R_9$ to form a second bond between $C_9$ and $C_{11}$, and the other of $R_{11-1}$ and $R_{11-2}$ is —H;

(C-II) $R_9$ is —H, —F, —Cl or Br and $R_{11}$ is $=$O or $\alpha$-$R_{11-3}$:$\beta$-$R_{11-4}$ where one of $R_{11-3}$ and $R_{11-4}$ is —H and the other of $R_{11-3}$ and $R_{11-4}$ is —H or —OH;

(C-III) $R_{11}$ is $\alpha$-H:$\beta$-O—, where $\beta$-O— is taken together with $R_9$ to form an epoxide between $C_9$ and $C_{11}$ in the $\beta$-configuration;

(D-I) $R_{16}$ is $R_{16-1}$:$R_{16-2}$ and $R_{17}$ is $R_{17-1}$:$R_{17-2}$, where one of $R_{16-1}$ and $R_{16-2}$ is —H and the other taken together with one of $R_{17-1}$ or $R_{17-2}$ forms a second bond between $C_{16}$ and $C_{17}$ and the other of $R_{17-1}$ and $R_{17-2}$ is —CO—CH$_2$—O—$R_{21}$ where $R_{21}$ is —H, —CO—(X$_1$)—COOR$_{21-1}$, where X$_1$ is —CH$=$CH— and —(CH$_2$)-$n_1$— where $n_1$ is 1–8 and where $R_{21-1}$ is —H or a cation;

(D-II) $R_{16}$ is $\alpha$-H:$\beta$-H, and where $R_{17}$ is $=$CH—CH$_2$—O—$R_{21}$ where $R_{21}$ is as defined above.

(D-III) $R_{16}$ is $=CH_2$ or $\alpha$-$R_{16-5}$:$\beta$-$R_{16-6}$ where $R_{16-5}$ is —H, —OH or —CH$_3$, $R_{16-6}$ is —H or —CH$_3$ with the proviso that one of $R_{16-5}$ or $R_{16-6}$ is —H, and where $R_{17}$ is $\alpha$-$R_{17-5}$:$\beta$-CO—CH$_2$13 O—$R_{21}$ where $R_{17-5}$ is —H or —OH, where $R_{21}$ is as defined above, which comprises contacting a $\Delta^4$-3-keto-21-hemiester steroid (I) where (D-I) $R_{16}$ is $R_{16-1}$:$R_{16-2}$ and $R_{17}$ is $R_{17-1}$:$R_{17-2}$, where one of $R_{16-1}$ and $R_{16-2}$ is —H and the other taken together with one of $R_{17-1}$ or $R_{17-2}$ forms a second bond between $C_{16}$ and $C_{17}$ and the other of $R_{17-1}$ and $R_{17-2}$ is —CO—CH$_{12}$—O—(X$_1$)—COOR$_{21-1}$, where X$_1$ and $R_{21-1}$ are as defined above;

(D-II) $R_{16}$ is $\alpha$-H:$\beta$-H, and where $R_{17}$ is $=$CH—CH$_2$—O—CO—(X$_1$)—COOR$_{21-1}$ where X$_1$ and $R_{21-1}$ are as defined above;

(D-III) $R_{16}$ is $=CH_2$ or $\alpha$-$R_{16-5}$:$\beta$-$R_{16-6}$ where $R_{16-5}$ is —H, —OH or —CH$_3$, $R_{16-6}$ is —H or —CH$_3$ with the proviso that one of $R_{16-5}$ or $R_{16-6}$ is —H, and where $R_{17}$ is $\alpha$-$R_{17-5}$:$\beta$-CO—CH$_2$—O—CO—(X$_1$(—COOR$_{21-1}$ where $R_{17-5}$ is —H or —OH and where X$_1$ and $R_{21-1}$ are as defined above, and where $R_6$, $R_9$ and $R_{11}$ are as defined above, with the steroid-1-dehydrogenase of *Arthrobacter simplex* or *Bacterium cyclooxydans*.

DETAILED DESCRIPTION OF THE INVENTION

The process of the present invention comprises contacting a $\Delta^4$-3-keto 21-hemiester steroid of formula (I) with either the steroid-1-dehydrogenase from *A. simplex* or *B. cyclooxydans* or with the cells of *A. simplex* or *B. cyclooxydans* containing steroid-1-dehydrogenase to produce the corresponding $\Delta^{1,4}$-3-keto steroid (II) as the 21-hemiester and/or free 21-hydroxy compound.

The $\Delta^4$-3keto steroidal 21-hemiester (I) starting materials are known to those skilled in the art or can be readily prepared from known compounds by methods known to those skilled in the art, see for example U.S. Pat. Nos. 3,025,311, 3,209,000 and 3,770,586. The $\Delta^4$-3- keto 21-hemiesters (I) can be made from either the corresponding $\Delta^4$-3-keto 21-halo or $\Delta^4$-3-keto 21-hydroxy steroids by simple well known displacement reactions. The $\Delta^4$-3-keto 21-halo, preferably the 21-chloro, steroid is reacted with a salt of the desired diacid to produce the $\Delta^4$-3-keto steroidal 21-hemiester (I). Alternatively, a $\Delta^4$-3-keto 21-hydroxy steroid is reacted with the appropriate anhydride or acid halide of the desired diacid to produce the $\Delta^4$-3-keto steroidal 21-hemiester (I).

With the $\Delta^4$-3-keto 21-hemiesters (I) it is preferred that $R_{6-1}$ be —H, —F, —CH$_3$ and =CH$_2$. It is preferred that the C-ring be either $\Delta^{9(11)}$ or have 11$\alpha$-OH, 11$\beta$-OH or have 2 hydrogen atoms at $C_{11}$. With regard to the D-ring it is preferred that the substitution at $C_{17}$ be =CH—CH$_2$—O—CO—(X$_1$)—COO—R$_{21-1}$ and $\alpha$-OH:$\beta$-CO—CH$_2$—O—CO—(X$_1$)—COOR$_{21-1}$. It is preferred that X$_1$ is —CH=CH— or —(CH)$_{n1}$— where n$_1$ is 2–4, more preferably 2. It is preferred that R$_{21}$ is succinate and fumarate. It is preferred that the cation be monovalent and be selected from the group consisting of sodium or potassium, ammonium or —H$^+$. The preferred steroidal portion of the hemiesters are selected from the group consisting of 17$\alpha$,21-dihydroxypregna-4,9(11)-diene-3,20-dione,
11$\beta$,21-dihydroxypregna-4,17(20)-dien-3-one,
11$\beta$,17$\alpha$,21-trihydroxy-6$\alpha$-methylpregn-4-ene-3,20-dione,
11$\beta$,21-dihydroxy-6$\alpha$-methylpregna-4,17(20)-dien-3-one,
11$\beta$,17$\alpha$,21-trihydroxypregn-4-ene-3,20-dione,
17$\alpha$,21-dihydroxy-6$\alpha$-methylpregna-4,9(11)-diene-3,20-dione,
17$\alpha$,21-dihydroxy-16$\beta$-methylpregna-4,9(11)-diene-3,20-dione,
6$\alpha$-fluoro-21-hydroxypregna-4,9(11),16-triene,3,20-dione,
21-hydroxypregna-4,9(11),16-triene-3,20-dione,
17$\alpha$,21-dihydroxy-16$\alpha$-methylpregna-4,9(11)-diene-3,20-dione. Most preferred is 11$\beta$,21-dihydroxypregna-4,17(20)-dien-3-one as the 21-hemisuccinate.

The microorganisms *A. simplex* and *B. cyclooxydans* are well known, see U.S. Pat. Nos. 2,837,464, 4,524,134 and 4,704,358. The process of the present invention may be practiced using the steroid-1-dehydrogenase activity from either organism in any of several forms. The enzyme from either organism is operable but it is preferred that *A. simplex* be used as the mnicrobial source. The bioconversion may be conducted with either cell-free steroid-1-dehydrogenase or with cells of the microorganisms. Preferably, whole microbial cells in the fermentation broth are used in the practice of the invention to avoid additional manufacturing steps. When using isolated cells, these may be used after collection and concentration from the nutrient medium by conventional means such as centrifugation, flocculation and filtration, precipitation and filtration or ultrafiltration. The isolated cells can be used in a wet state or can be immobilized by standard techniques, such as entrapment in collagen, alginate or carrageenin as described in Methods in Enzymology, Vol. XLIV, p. 11–317, (1976), Academic Press, Inc., New York or can be dried by treatment with a lower alcohol or alkanone such as acetone as described in U.S. Pat. No. 3,360,439, by vacuum-drying with heat, by freeze-drying, by air-drying with heat or by spray-drying as described in U.S. Pat. Nos. 4,524,134 and 4,704,358. Steroid-1-dehydrogenase activity in a cell-free form can also be used in solution or as an immobilized enzyme to catalyze steroid-1-dehydrogenation. It should be understood that the subject process covers the use of any form of steroid-1-dehydrogenase preparation from *A. simplex* and *B. cyclooxydans* for the steroid bioconversion of $\Delta^4$-3-keto 21-hemiester steroids (I) to the corresponding $\Delta^{1,4}$-3-keto steroids (II).

The bioconversion is accomplished by exposure of the steroid substrate, $\Delta^4$-3-keto 21-hemiester steroids (I), to the preparation containing steroid-1-dehydrogenase activity in a predominantly aqueous system with a pH range of 6 to 10, preferably 7 to 8. The aqueous system can contain less than about five per cent of a water-miscible organic solvent. Suitable water-miscible organic solvents include, for example, dimethyl sulfoxide, dimethylformamide, methanol, ethanol, acetone and the like. Optionally, a water-immiscible organic solvent can be added (provided that it is non-toxic to the steroid-1-dehydrogenase activity) in an amount of from about 2 to about 50%. Suitable water-immiscible organic solvents include toluene, benzene, butyl acetate, heptane, methylene chloride and the like; preferred is toluene. The organic solvents can be used to dissolve or suspend the $\Delta^4$-3-keto 21-hemiester steroid substrate (I) or an exogenous electron carrier prior to its/their addition to the steroid-1-dehydrogenase preparation. It is preferred that the contacting of the steroid substrate take place in the presence of an exogenous electron carrier. It is not necessary to have the exogenous electron carrier present with all the $\Delta^4$-3-keto 21-hemiester substrates (I) as is known to those skilled in the art, but it is preferred. It is particularly preferred when the bioconversion is performed cell free or with dried cells. The exogenous electron carrier can be added to stimulate steroid-1-dehydrogenation and/or to prevent other steroid-degrading activities in preparations where these activities have not been previously eliminated. It is preferred that the exogenous electron carrier be selected from the group consisting of menadione, menadione bisulfite, 1,4-naphthoquinone, phenazine methosulfate, phenazine ethosulfate, dichlorophenol indophenol, and cytochrome c. It is more preferred that the exogenous electron carrier be menadione, menadione bisulfite or 1,4-naphthoquinone. The exogenous electron carrier is used in catalytic amounts from about 0.01 g/l in the manner described in U.S. Pat. No. 4,524,134, to about 3.0 g/l, provided hydrogen peroxide accumulation is minimized. It is preferred that about 0.10 to about 1.0 g/l be used. During the biotransformation process the mixture preferably has access to molecular oxygen and is stirred. The temperature is maintained between about 5° and about 45°, preferably in the range of about 25° and 35°.

The type of bioconversion procedure to be used to dehydrogenate a specific $\Delta^4$-3-keto 21-hemiester steroid substrate (I) will vary dependent on the structure and nature of the particular steroid. For example, the substrate discussed in Example 1 is bioconverted to completion using whole cells in a fermentation broth, whereas its conversion is substantially poorer using an equivalent amount of heat-dried cells of *A. simplex*. The optimum type and level of the enzyme preparation, optimum substrate concentration, time of substrate addition and duration of the bioconversion can be readily determined in each individual steroid-1-dehydrogenation reaction with routine preliminary experimentation within the expertise of one of ordinary skill in the art. Most of the $\Delta^4$-3-keto 21-hemiester steroid substrates (I) bioconvert well only in a system which is about 95% or greater aqueous. Not all the $\Delta^4$-3-keto 21-hemiester steroids (I) will work well under all of the above conditions. Some work better with only an aqueous system, some with a water-miscible or water-immiscible organic solvent; some work better with fermentation cells and others with dried cells, etc.

Known steroid-1-dehydrogenation processes with *A. simplex* cells in fermentation broths use $\Delta^4$-3-keto steroid substrates which at the $C_{21}$ position have 21-hydroxy or 21-monocarboxylic esters functionality, preferably acetic acid esters. The substrate concentrations of these 21-hydroxy- or 21-acyloxy- $\Delta^4$-3-keto steroids in the fermentation media is from about 1.5 to about 5 g/liter, as described in U.S. Pat. No. 2,837,464. Known processes to 1-dehydrogenate $\Delta^4$-3-keto steroid 21-hemiesters (I) use substrate concentration from about 2 to about 10 g/liter based on the 21-ester weight or from about 1.4 to about 7.1 g/liter based on the 21-hydroxy steroid parent, see U.S. Pat. No. 3,770,586. The process of the present invention using *A. simplex* permits the advantageous use of higher substrate levels in bioconversions performed with fermentation broths using 21-dicarboxylic acid ester $\Delta^4$-3-keto 21-hemiester steroid substrates (I) and a complete reaction in a shorter time period.

The process of the present invention permits the advantageous use of higher substrate concentrations with the advantageous result of shorter reaction times. The process of the present invention permits use of $\Delta^4$-3-keto 21-hemiester steroid (I) concentrations of about 4 to about 30 g/l based on the non-esterified $\Delta^4$-3-keto steroid. Below about 4 g/l is operable but not commercially important. Above about 30 g/l the residuals increase to a point where it is preferable to perform the reaction at lower substrate levels. It is preferred that the $\Delta^4$-3-keto steroid (I) concentration be equivalent to about 4 to about 12 g/l based on the parent 21-hydroxy steroid.

The process of the present invention provides the $\Delta^{1,4}$-3-keto steroids (II) in improved yields and in less time than previously required. The reaction producing the $\Delta^{1,4}$-3-keto steroids (II) is complete in about 4 to about 72 hr. Present steroid-1-dehydrogenation processes usually average about 120 hr using hemiesters with *S. affinis*, see U.S. Pat. No. 3,770,586.

When the $\Delta^4$-3-keto 21-hemiester steroid starting material has been converted to the corresponding $\Delta^{1,4}$-3-keto steroid (II) product it is isolated by means well known to those skilled in the art.

The $\Delta^{1,4}$-3-keto steroid (II) products are useful as intermediates in the production of steroid pharmaceuticals.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3-C(=Z_1)H$. Groups $R_i$ and $R_j$ would represent monovalent variable substituents if attached to the formula $CH_3-CH_2-C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalaent or bivalent) at the $C_6$ position.

Chemical formulas or portions thereof drawn in a linear fashion represent atoms in a linear chain. The symbol "—" in general represents a bond between two atoms in the chain. Thus $CH_3-O-CH_2-CH(R_i)-CH_3$ represents a 2-substituted-1-methoxypropane compound. In a similar fashion, the symbol "=" represents a double bond, e.g., $CH_2=C(R_i)-O-CH_3$, and the symbol "57" represents a triple bond, e.g., $HC\equiv C-CH(R_i)-CH_2-CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N^*=C(CH_3)-CH=CCl-CH=C^*H$ with the convention that the atoms marked with an asterisk (*) are bonded to each other resulting in the formation of a ring. Likewise, the cyclic molecular fragment, 4-(ethyl)-1-piperazinyl can be represented by $-N^*-(CH_2)_2-N(C_2H_5)-CH_2-C^*H_2$.

A cyclic (ring) structure for any compound herein defines an orientation with respect to the plane of the ring for substituents attached to each carbon atom of the cyclic compound. In formulas depicting such compounds, a substituent attached to a carbon atom below the plane of the ring is identified as being in the alpha ($\alpha$) configuration and is indicated by a broken, dashed or dotted line attachment to the carbon atom, i.e., by the symbol "- - -" or ". . .". The corresponding substituent attached above the plane of the ring is identified as being in the beta ($\beta$) configuration. When a variable substituent is bivalent, the valences may be taken together or separately or both in the definition of the variable. For example, a variable $R_i$ attached to a carbon atom as $-C(=R_i)-$ might be bivalent and be defined as oxo or keto (thus forming a carbonyl group (—CO—) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\beta$-$R_{i-j}$ and $\beta$-$R_{i-k}$ are attached to the carbon atom to yield $-C(\alpha-R_{i\text{-}j})(\beta-R_{i\text{-}k})-$. For example, when the bivalent variable $R_6$, $-C(=R_6)-$ is defined to consist of two monovalent variable substituents, two monovalent variable substituents are $\alpha-R_{6\text{-}1}:\beta-R_{6\text{-}2}, \ldots \alpha-R_{6\text{-}9}:\beta-R_{6\text{-}10}$, etc. yielding $-C(\alpha-R_{6\text{-}1})(\beta-R_{6\text{-}2})-, \ldots -C(\alpha-R_{6\text{-}9})(\beta-R_{6\text{-}10})-$, etc. Likewise, for the bivalent variable $R_{11}$, $-C(=R_{11})-$, two monovalent variable substituents are $\alpha-R_{11\text{-}1}:\beta-R_{11\text{-}2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula $-C_1(R_i)H-C_2(R_j)H-$ ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa ($-O-$) and the formula thereby describes an epoxide. When $R_i$ and $R_j$ are taken together to form a more complex entity, such as the group $-X-Y-$, then the orientation of the entity is such that $C_1$ in the above formula is bonded to X and $C_2$ is bonded to Y. Thus, by convention the designation ". . . $R_i$ and $R_j$ are taken together to form $-CH_2-CH_2-O-CO-$ . . ." means a lactone in which the carbonyl is bonded to $C_2$. However, when designated ". . . $R_j$ and $R_i$ are taken together to form $-CH_2-CH_2-O-CO-$ the convention means a lactone in which the carbonyl is bonded to $C_1$.

The carbon atom content of variable substituents is indicated in one of two ways. The first method uses a prefix to the entire name of the variable such as "$C_1-C_4$", where both "1" and "4" are integers representing the minimum and maximum number of carbon atoms in the variable. The prefix is separated from the variable by a space. For example, "$C_1-C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2-C_4$ alkoxycarbonyl describes a group $CH_3-(CH_2)_n-O-CO-$ where n is zero, one or 2. By the second method the carbon atom content of only each portion of the definition is indicated separately by enclosing the "Ci-Cj" designation in parentheses and placing it immediately (no intervening space) before the portion of the definition being defined. By this optional convention ($C_1-C_3$)alkoxycarbonyl has the same meaning as $C_2-C_4$ alkoxycarbonyl because the "$C_1-C_3$" refers only to the carbon atom content of the alkoxy group. Similarly while both $C_2-C_6$ alkoxyalkyl and ($C_1-C_3$)alkoxy($C_1-C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.
HPLC refers to high pressure liquid chromatography.
DMF refers to dimethylformamide.
When solvent pairs are used, the ratios of solvents used are volume/volume (v/v).
*A. simplex* refers to *Arthrobacter simplex*.
*B. cyclooxydans* refers to *Bacterium cyclooxydans*.
The concentrations of $\Delta^4$-3-keto 21-hemiester steroid substrates (I) are expressed as grams/liter, the weight (g) being expressed as the amount of the corresponding 21-hydroxy steroid.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

*A. simplex* Bioconversion of
11β,21-Dihydroxypregna-4,17(20)-diene-3-one
21-Hemisuccinate Potassium Salt (I)

A. Primary Microorganism Seed Development Stage

Cells from a culture of *Arthrobacter simplex* (UC582, ATCC 6946), maintained on nutrient agar slants, are resuspended in sterile water (5 ml) and used to inoculate 300 ml primary seed medium which is composed of nutrient broth (12 g/liter of Difco brand), which had been sterilized at 121° for 30 minutes prior to inoculation.

The mixture is incubated in 1 liter shake flasks at 28° on a rotary shaker (250 rpm, 2 inch throw) for two days.

B. Secondary Seed Development Seed Stage

The growth medium used for the secondary proliferation of the microorganism consists of an aqueous mixture of the following nutrient materials:

| | Concentration of Ingredients | Supplier |
|---|---|---|
| Dried Corn steep liquor (Solulys A) | 20 g/l | Roquette Freres |
| Lard oil (No. 2) | 15 g/l | Geo. Pfau & Son |
| Silicone defoamer (SAG-471) | 0.1 ml/l | Union Carbide |
| Cortisone acetate | 0.1 g/l | The Upjohn Company |

The pH of the medium is adjusted to pH 7.0 with reagent grade sodium hydroxide prior to sterilization, as described above. Two shake flasks (300 ml) from the primary stage above are used to inoculate a 250 liter secondary seed medium. The fermentor is run at about 28°, at an agitation rate of 280 rpm, an aeration rate of 100 standard liters per minute (slm) and at 5 psi backpressure. The secondary seed stage is incubated for two days.

C. The Fermentation (Reaction) Stage of the Process of this Invention

An aqueous medium containing 20 g/l of dried corn steep liquid (Solulys A), 20 g/l of lard oil No. 2, 0.1 g/l of cortisone acetate and 0.2 ml/l of a silicone defoamer (SAG-471 - Union Carbide) is adjusted to pH 6.0 with sodium hydroxide prior to sterilization of the mixture. The resulting medium is sterilized at 121° for 30 min in a fermenter having a working volume of 250 liters. The medium in the tank is stirred at a temperature of 28°, an agitation rate of 280 rpm, an aeration rate of 25 slm and with a 5 psi backpressure. The fermentor contents are inoculated with 5 percent by volume of the final fermented volume of a 48 hour growth (secondary seed medium from above) of *Arthrobacter simplex* (ATCC 6946). The resulting culture mixture is allowed to grow for 36 hours at which time the pH was adjusted to 7.5 and maintained by an automatic addition of sulfuric acid or sodium hydroxide. Menadione is added after the pH adjustment, to a final concentration of 0.17 g/l. The $\Delta$-3-keto 21-hemiester steroid substrate (I), 11$\beta$,21-dihydroxypregna-4,17(20)-diene-3-one 21-hemisuccinate potassium salt (I) is added in DMF to give a final concentration of 11.35 g/l (which is equivalent to 8 g/l of the corresponding 21-hydroxy $\Delta^4$-3-keto steroid). This mixture is incubated for 48 hours.

The completeness of the reaction is determined by an HPLC assay. The products, a mixture of 11$\beta$,21-dihydroxypregna-1,4,17(20)-triene-3-one (II) and 11$\beta$,21-dihydroxypregna-1,4,17(20)-triene-3-one 21-hemisuccinate (II) are hydrolyzed to 11$\beta$-21-dihydroxypregna-1,4,17(20)-triene-3-one (II) by base. This is followed by filtration of the mixture where the $\Delta^{1,4}$-3-keto steroid (II) is retained in the filter cake and subsequently extracted with aqueous acetone and crystallized by procedures well known in the art. The products were identified by comparison with known samples by HPLC on a silica based C-8 column, 25 cm, eluting with a mobile phase of acetonitrile/water/acetic acid (40/60/0.1). The retention time of the 21-hydroxy compound is 12.5 min. and of the 21-hemisuccinate is 28.5 min.

EXAMPLES 2–20

Following the general procedure of EXAMPLE 1 and making non-critical variations but starting with the $\Delta^4$-3-keto 21-hemiester steroids (I) of Column A below, the corresponding $\Delta^4$-3-keto 21-hemiester steroids (I) of Column A below, the corresponding $\Delta^{1,4}$ steroids (II) are obtained either as the free 21-alcohol or the 21hemiester or a mixture thereof.

| EXAMPLE | Column A |
|---|---|
| 2 | 17$\alpha$,21-dihydroxypregna-4,9(11)-diene-3,20-dione 21-hemisuccinate |
| 3 | 11$\beta$,17$\alpha$,21-trihydroxy-6$\alpha$-methylpregn-4-ene-3,20-dione 21-hemisuccinate potassium salt |
| 4 | 11$\beta$,21-dihydroxy-6$\alpha$-methylpregna-4,17(20)-dien-3-one 21-hemisuccinate sodium salt |
| 5 | 11$\beta$,17$\alpha$,21-trihydroxypregn-4-ene-3,20-dione 21-hemisuccinate triethylamine salt |
| 6 | 17$\alpha$,21-dihydroxy-6$\alpha$-methylpregna-4,9(11)-diene-3,20-dione 21-hemisuccinate |
| 7 | 17$\alpha$,21-dihydroxy-16$\beta$-methylpregna-4,9(11)-diene-3,20-dione 21-hemisuccinate sodium salt |
| 8 | 6$\alpha$-fluoro-21-hydroxypregna-4,9(11),16-triene-3,20-dione 21-hemisuccinate potassium salt |
| 9 | 21-hydroxypregna-4,9(11),16-triene-3,20-dione 21-hemisuccinate |
| 10 | 17$\alpha$,21-dihydroxy-16$\alpha$-methylpregna-4,9(11)-diene-3,20-dione 21-hemisuccinate |
| 11 | 11$\beta$,21-dihydroxypregna-4,17(20)-dien-3-one 21-hemifumarate |
| 12 | 17$\alpha$,21-dihydroxypregna-4,9(11)-diene-3,20-dione 21-hemioxylate |
| 13 | 11$\beta$,17$\alpha$,21-trihydroxy-6$\alpha$-methylpregn-4-ene-3,20-dione 21-hemimaleate sodium salt |
| 14 | 11$\beta$,21-dihydroxy-6$\alpha$-methylpregna-4,17(20)-dien-3-one 21-hemiglutarate sodium salt |
| 15 | 11$\beta$,17$\alpha$,21-trihydroxypregn-4-ene-3,20-dione 21-hemiadipate triethylamine salt |
| 16 | 17$\alpha$,21-dihydroxy-6$\alpha$-methylpregna-4,9(11)-diene-3,20-dione 21-hemifumarate sodium salt |
| 17 | 17$\alpha$,21-dihydroxy-16$\beta$-methylpregna-4,9(11)-diene-3,20-dione 21-hemimaleate |
| 18 | 6$\alpha$-fluoro-21-hydroxypregna-4,9(11),16-triene-3,20-dione 21-hemiglutarate |
| 19 | 21-hydroxypregna-4,9(11),16-triene-3,20-dione 21-hemioxylate |
| 20 | 17$\alpha$,21-dihydroxy-16$\alpha$-methylpregna-4,9(11)-diene-3,20-dione 21-hemimalate |

EXAMPLE 21

*A. simplex* (dried cell) Bioconversion of 6$\alpha$-fluoro-21-hydroxypregna-4,9(11)16(17)-triene-3,20-dione 21-hemisuccinate (I)

Following the general procedures of U.S. Pat. No. 4,524,134, and making non-critical variations 1.0 gram of dried *A. simplex* cells are suspended in potassium phosphate buffer (0.05M, 100 ml, pH 7.5). Menadione (8.6 mg) is dissolved in ethanol (1 ml) and is added to the cell suspension. The $\Delta^4$-3-keto 21-hemiester steroid substrate (I), 6$\alpha$-fluoro-21-hydroxypregna-4,9(11),16(17)-triene-3,20-dione 21-hemisuccinate (I) is dissolved in DMF and added to the shake flask to a final steroid concentration of 4.0 g/l (based on the corresponding 21-hydroxy steroid) and a final DMF concentration of about 5 percent. Replicate flasks are incubated on a rotary shaker at 31° for three days. Analysis of the bioconversion mixture by HPLC indicates that 99 percent of the $\Delta^4$-3-keto steroid 21-hemiester substrate (I) is dehydrogenated to the corresponding $\Delta^1$ product and is present as a mixture of the 21-hemisuccinate (II) and 21-hydroxy forms (II). The products were identified by comparison with known samples by HPLC, on a silica based C-8 column, eluting with acetonitrile/THF/water/acetic acid (9/31/60/0.3), retention time of the 21-hydroxy compound is 8.19 min, the 21-hemisuccinate is 12.51 and the substrate is 16.25 min.

EXAMPLE 22

*B. cyclooxydans* Bioconversion of 11$\beta$,17$\beta$,21-trihydroxy-6$\alpha$-methylpregna-4-ene-3,20-dione 21 hemisuccinate succinate (I)

Following the general procedure of U.S. Pat. No. 4,704,358 and making non-critical variations but starting with 11$\beta$,17$\alpha$,21-trihydroxy-6$\alpha$-methylpregna-4-ene-3,20-dione 21-hemisuccinate (I) and using *B. cyclooxydans*, the title compound is obtained. The bioconversion is monitored by thin layer chromatography of butyl acetate extracts and known standards on a silica gel

CHART A

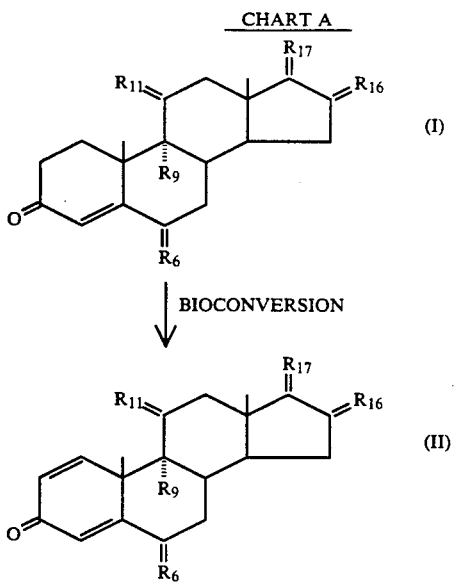

We claim:

1. A process for the production of a $\Delta^{1,4}$-3-keto 21-hemiester steroid of formula (II)

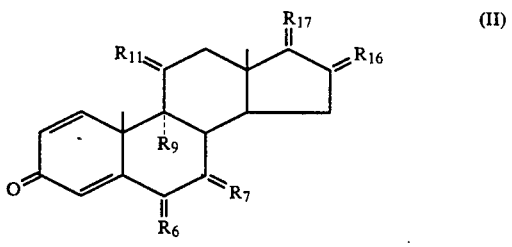

where (B-I) $R_6$ is $=CH_2$ or $\alpha$-$R_{6-1}$:$\beta$-H where $R_{6-1}$ is —H, —F or —CH$_3$, $R_7$ is $\alpha$-H:$\beta$-H;

(B-II) $R_6$ is $R_{6-3}$:$R_{6-4}$ and $R_7$ is $R_{7-3}$:$R_{7-4}$ where one of $R_{6-3}$ and $R_{6-4}$ taken together with one of $R_{7-3}$ and $R_{7-4}$ form a second bond between $C_6$ and $C_7$, the other of $R_{6-3}$ and $R_{6-4}$ is —CH$_3$ and the other of $R_{7-3}$ and $R_{7-4}$ is —H;

(C-I) $R_{11}$ is $\alpha$-$R_{11-1}$:$\beta$-$R_{11-2}$ where one of $R_{11-1}$ and $R_{11-2}$ is taken together with $R_9$ to form a second bond between $C_9$ and $C_{11}$, and the other of $R_{11-1}$ and $R_{11-2}$ is —H;

(C-II) $R_9$ is —H, —F, —Cl or —Br and $R_{11}$ is =O or $\alpha$-$R_{11-3}$:$\beta$-$R_{11-4}$ where one of $R_{11-3}$ and $R_{11-4}$ is —H and the other of $R_{11-3}$ and $R_{11-4}$ is —H or —OH;

(CIII) $R_{11}$ is $\alpha$-H:$\beta$-O—, where $\beta$-O— is taken together with $R_9$ to form an epoxide between $C_9$ and $C_{11}$ in the $\beta$- configuration;

(D-I) $R_{16}$ is $R_{16-1}$:$R_{16-2}$ and $R_{17}$ is $R_{17-1}$:$R_{17-2}$, where one of $R_{16-1}$ and $R_{16-2}$ is —H and the other taken together with one of $R_{17-1}$ or $R_{17-2}$ forms a second bond between $C_{16}$ and $C_{17}$ and the other of $R_{17-1}$ and $R_{17-2}$ is —CO—CH$_2$—O—R$_{21}$ where $R_{21}$ is —H, —CO—(X-1)—COOR$_{21-1}$, where $X_1$ is —CH=CH— and —(CH$_2$)$_{n1}$— where $n_1$ is 1-8 and where $R_{21-1}$ is —H or a cation;

(D-II) $R_{16}$ is $\alpha$-H:$\beta$-H, and where $R_{17}$ is =CH—CO—2—O—R$_{21}$ where $R_{21}$ is as defined above;

(D-III) $R_{16}$ is =CH$_2$ or $\alpha$-$R_{16-5}$:$\beta$-$R_{16-6}$ where $R_{16-5}$ is —H, —OH or —CH$_3$, $R_{16-6}$ is —H or —CH$_3$ with the proviso that one of $R_{16-5}$ or $R_{16-6}$ is —H, and where $R_{17}$ is $\alpha$-$R_{17-5}$:$\beta$-CO—CH$_2$—O—R$_{21}$ where $R_{17-5}$ is —H or —OH, where $R_{21}$ is as defined above, which comprises contacting a $\Delta^4$-3-keto 21-hemiester steroid of formula (I)

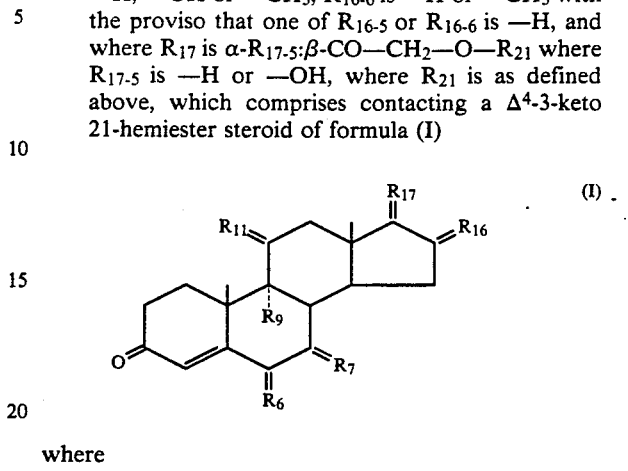

where (D-I) $R_{16}$ is $R_{16-1}$:$R_{16-2}$ and $R_{17}$ is $R_{17-1}$:$R_{17-2}$, where one of $R_{16-1}$ and $R_{16-2}$ is —H and the other taken together with one of $R_{17-1}$ or $R_{17-2}$ forms a second bond between $C_{16}$ and $C_{17}$ and the other of $R_{17-1}$ and $R_{17-2}$ is —CO—CH$_2$—O—CO—(X-1)—COOR$_{21-1}$, where $X_1$ and $R_{21-1}$ are as defined above;

(D-II) $R_{16}$ is $\alpha$-H:$\beta$-H, and where $R_{17}$ is =CH—CH$_2$—O—CO—(X$_1$)—COOR$_{21-1}$ where $X_1$ and $R_{21-1}$ are as defined above;

(D-III) $R_{16}$ is =CH$_2$ or $\alpha$-$R_{16-5}$:$R_{16-6}$ where $R_{16-5}$ is —H, —OH or —CH$_3$, $R_{16-6}$ is —H or —CH$_3$ with the proviso that one of $R_{16-5}$ or $R_{16-6}$ is —H, and where $R_{17}$ is $\alpha$-$R_{17-5}$:$\beta$-CO—CH$_2$—O—CO—(X-1)—COOR$_{21-1}$ where $R_{17-5}$ is —H or —OH and where $X_1$ and $R_{21-1}$ are as defined above, and where $R_6$, $R_9$ and $R_{11}$ are as defined above, with the *Arthrobacter simplex*, *Bacterium cyclooxydans*, or the steroid $\Delta^2$-dehydrogenase therefrom.

2. A process for the production of a $\Delta^{1,4}$-3-keto steroid (II) according to claim 1 where the process is performed in the presence of an effective amount of an exogenous electron carrier to perform the dehydrogenation.

3. A process for the production of a $\Delta^{1,4}$-3-keto steroid (II) according to claim 2 where the exogenous electron carrier is selected from the group consisting of menadione, menadione bisulfite, 1,4-naphthoquinone, phenazine methosulfate, phenazine ethosulfate, dichlorophenol indophenol and cytochrome c.

4. A process for the production of a $\Delta^{1,4}$-3-keto steroid (II) according to claim 3 where the exogenous electron carrier is menadione, menadione bisulfite and 1,4-naphthoquinone.

5. A process for the production of a $\Delta^{1,4}$-3-keto steroid (II) according to claim 1 where $R_6$ is —H:—H, —F:—H, —CH$_3$:—H and =CH$_2$.

6. A process for the production of a $\Delta^{1,4}$-3-keto steroid (II) according to claim 1 where one of $R_{11-3}$ and $R_{11-4}$ is —H and the other is —H or —OH.

7. A process for the production of a $\Delta^{1,4}$-3-keto steroid (II) according to claim 1 were $R_{11}$ is $\alpha$-$R_{11-1}$:$\beta$-$R_{11-2}$ where one of $R_{11-1}$ and $R_{11-2}$ is taken together with $R_9$ to form a second bond between $C_9$ and $C_{11}$, and the other of $R_{11-1}$ and $R_{11-2}$ is —H.

8. A process for the production of a $\Delta^{1,4}$-3-keto steroid (II) according to claim 1 where $R_{17}$ is $=$CH—CH$_2$—O—CO—(X$_1$)—COO—R$_{21-1}$.

9. A process for the production of a $\Delta^{1,4}$-3-keto steroid (II) according to claim 1 where $R_{17}$ is $\alpha$-OH:$\beta$-CH$_2$—O—CO—(X$_1$)—COOR$_{21-1}$.

10. A process for the production of a $\Delta^{1,4}$-3-keto steroid (II) according to claim 1 where $X_1$ is —CH=CH—.

11. A process for the production of a $\Delta^{1,4}$-keto steroid (II) according to claim 1 where $X_1$ is —(CH$_2$)$_{n1}$—.

12. A process for the production of a $\Delta^{1,4}$-keto steroid (II) according to claim 1 where $n_1$ is 2–4.

13. A process for the production of a $\Delta^{1,4}$-3-keto steroid (II) according to claim 1 where $n_1$ is 2.

14. A process for the production of a $\Delta^{1,4}$-3-keto steroid (II) according to claim 1 where the cation is monovalent.

15. A process for the production of a $\Delta^{1,4}$-3-keto steroid (II) according to claim 14 where the monovalent cation is sodium, potassium, ammonium or —H$^+$.

16. A process according to claim 1 where the $\Delta^4$-3-keto 21-hemiester steroid (I) is selected from the group consisting of the hemiesters (—CO—X$_1$—COOR$_{21-1}$) at C$_{21}$ of the following $\Delta^4$-3-keto steroids
17$\alpha$,21-dihydroxypregna-4,9(11)-diene-3,20-dione,
11$\beta$,21-dihydroxypregna-4,17(20)-dien-3-one,
11$\beta$,17$\alpha$,21-trihydroxy-6$\alpha$-methylpregn-4-ene-3,20-dione,
11$\beta$,21-dihydroxy-6$\alpha$-methylpregna-4,17(20)-dien-3-one,
11$\beta$,17$\alpha$,21-trihydroxypregn-4-ene-3,20-dione,
17$\alpha$,21-dihydroxy-6$\alpha$-methylpregna-4,9(11)-diene-3,20-dione,
17$\alpha$,21-dihydroxy-16$\beta$-methylpregna-4,9(11)-diene-3,20-dione,
6$\alpha$-fluoro-21-hydroxypregna-4,9(11)16-triene,3,20-dione,
21-hydroxypregna-4,9(11),16-triene-3,20-dione,
17$\alpha$,21-dihydroxy-16$\alpha$-methylpregna-4,9(11)-diene-3,20-dione.

17. A process for the production of a $\Delta^{1,4}$-3-keto steroid (II) according to claim 1 where the contacting is performed with cells of *A. simplex* or *B. cyclooxydans*.

18. A process for the production of a $\Delta^{1,4}$-3-keto steroid (II) according to claim 3 where the contacting with *A. simplex* or *B. cyclooxydans* is with dried cells of *A. simplex* or *B. cyclooxydans*.

19. A process for the production of a $\Delta^{1,4}$-3-keto steroid (II) according to claim 18 where the dried cells are air or heat dried.

20. A process for the production of a $\Delta^{1,4}$-keto steroid (II) according to claim 1 where the contacting with *A. simplex* or *B. cyclooxydans* is with viable reproducing cells under aerobic fermentation conditions in an aqueous nutrient medium.

21. A process for the production of a $\Delta^{1,4}$-3-keto steroid (II) according to claim 2 where the steroid $\Delta^1$-dehydrogenase is in the form of a cell free preparation.

* * * * *

UNITED STATES PATENT AND TRADEMARK OFFICE
CERTIFICATE OF CORRECTION

PATENT NO. : 5,225,335
DATED : July 6, 1993
INVENTOR(S) : Leo A. Kominek et al

It is certified that error appears in the above-indentified patent and that said Letters Patent is hereby corrected as shown below:

On the title page, item [63], should read -- A continuation of Serial No. 025,127, filed 12 March 1987--.

Signed and Sealed this

Seventeenth Day of January, 1995

Attest:

BRUCE LEHMAN

*Attesting Officer*  *Commissioner of Patents and Trademarks*